United States Patent
Hada et al.

[11] Patent Number: 5,990,338
[45] Date of Patent: Nov. 23, 1999

[54] NEGATIVE-WORKING CHEMICAL-SENSITIZATION PHOTORESIST COMPOSITION

[75] Inventors: Hideo Hada, Hiratsuka; Yoshiki Sugeta, Yokohama; Hiroyuki Yamazaki; Hiroshi Komano, both of Koza-gun, all of Japan

[73] Assignee: Tokyo Ohka Kogyo Co., Ltd., Japan

[21] Appl. No.: 09/179,817

[22] Filed: Oct. 28, 1998

Related U.S. Application Data

[62] Division of application No. 08/791,814, Jan. 30, 1997, Pat. No. 5,892,095.

[30] Foreign Application Priority Data

Feb. 2, 1996 [JP] Japan ................................. 8-018008

[51] Int. Cl.$^6$ .................................................. C07C 255/00
[52] U.S. Cl. ........................ 558/388; 430/325; 430/328; 430/330; 430/332; 430/334
[58] Field of Search .................... 430/325, 328, 430/332, 334, 330; 558/338

[56] References Cited

U.S. PATENT DOCUMENTS

| | | | |
|---|---|---|---|
| 4,451,286 | 5/1984 | Martin | 71/107 |
| 4,466,822 | 8/1984 | Martin | 558/391 X |
| 4,540,598 | 9/1985 | Berner et al. | 427/54.1 |
| 4,548,756 | 10/1985 | Martin | 558/390 |
| 4,566,901 | 1/1986 | Martin | 558/391 X |
| 4,736,055 | 4/1988 | Dietliker et al. | 560/13 |
| 4,800,230 | 1/1989 | Roper | 558/380 |
| 5,358,968 | 10/1994 | Oberdorf et al. | 514/620 |
| 5,442,063 | 8/1995 | Takase et al. | 544/333 |
| 5,489,605 | 2/1996 | Oberdorf et al. | 514/374 |
| 5,696,161 | 12/1997 | Kirstgen et al. | 514/421 |
| 5,892,095 | 4/1999 | Hada et al. | 558/388 |

FOREIGN PATENT DOCUMENTS

| | | |
|---|---|---|
| 0 044 115 | 1/1982 | European Pat. Off. . |
| 0 241 423 | 10/1987 | European Pat. Off. . |
| 0 361 907 | 4/1990 | European Pat. Off. . |
| 0 571 330 | 11/1993 | European Pat. Off. . |

*Primary Examiner*—Floyd D. Higel
*Attorney, Agent, or Firm*—Wenderoth, Lind & Ponack, L.L.P.

[57] ABSTRACT

Disclosed is a novel positive-working or negative-working chemical-sensitization photoresist composition useful in the photolithographic patterning works for the manufacture of electronic devices. The photoresist composition is characterized by a unique acid-generating agent capable of releasing an acid by the pattern-wise exposure of the resist layer to actinic rays so as to increase or decrease the solubility of the resist layer in an aqueous alkaline developer solution. The acid-generating agent proposed is a novel cyano group-containing oxime sulfonate di- or triester compound represented by the general formula $$A[C(CN)=N-O-SO_2-R]_n,$$

in which each R is, independently from the others, an unsubstituted or substituted monovalent hydrocarbon group such as alkyl groups, A is a divalent or tervalent organic group or, preferably, phenylene group and the subscript n is 2, when A is a divalent group, or 3, when A is a tervalent group or, preferably 2. Since more than one of sulfonic acid molecules are released from one molecule of the sulfonate compound by the exposure to actinic rays, the chemical-sensitization photoresist composition exhibits high photosensitivity.

6 Claims, No Drawings

NEGATIVE-WORKING CHEMICAL-SENSITIZATION PHOTORESIST COMPOSITION

This is a divisional of Ser. No. 08/791,814, filed Jan. 30, 1997, now U.S. Pat. No. 5,892,095.

BACKGROUND OF THE INVENTION

The present invention relates to a novel chemical-sensitization photoresist composition or, more particularly, to a chemical-sensitization photoresist composition used in the photolithographic patterning process for the manufacture of various kinds of electronic devices capable of giving a patterned resist layer having excellent cross-sectional profile and high fidelity as well as high heat resistance of the patterned resist layer with high photosensitivity and exposure dose latitude. The invention also relates to a novel oxime sulfonate compound useful as an acid-generating agent in the chemical-sensitization photoresist composition.

It is a trend in recent years in the photolithographic patterning works for the manufacture of various kinds of electronic devices such as semiconductor devices and liquid crystal display panels that the patterning work is performed by using a chemical-sensitization photoresist composition which contains a relatively small amount of a compound capable of releasing an acid by irradiation with actinic rays and a resinous ingredient susceptible to the changes of solubility behavior in a developer solution induced by the acid. Chemical-sensitization photoresist compositions in general are characterized by high sensitivity to actinic rays and excellent pattern resolution.

Chemical-sensitization photoresist compositions are classified into positive-working compositions and negative-working compositions depending on the type of the solubility change of the resinous ingredient to an aqueous alkaline developer solution by the radiation-generated acid. Namely, the alkali-solubility of the resist layer of a positive-working photoresist composition is increased while the alkali-solubility is decreased in the negative-working photoresist composition by exposure to actinic rays.

The film-forming resinous ingredient in a positive-working photoresist composition is typically an alkali-soluble polyhydroxystyrene resin, of which at least a part of the hydroxy groups are substituted by acid-dissociable substituent groups such as tert-butoxycarbonyl groups, tetrahydropyranyl groups and the like, so as to decrease the solubility of the resin in an alkaline developer solution. In the negative-working photoresist composition, on the other hand, the film-forming resinous ingredient is a combination of an acid-induced crosslinking agent such as melamine resins and urea resins with a polyhydroxystyrene resin, optionally substituted by the above-mentioned acid-dissociable solubility-reducing substituent groups for a part of the hydroxy groups.

The other essential ingredient in the chemical-sensitization photoresist compositions is a compound capable of releasing an acid by irradiation with actinic rays, of which various classes of compounds have been heretofore proposed and actually tested. A class of the most promising acid-generating agents includes oxime sulfonate compounds, in particular, having a cyano group in the molecule. Several compositions containing an oxime sulfonate compound and methods using the same are proposed. For example, European Patent Application 44115 A1 discloses a heat-curable coating solution containing an acid-curable amino resin and an oxime sulfonate compound. Japanese Patent Kokai 60-65072 discloses a method in which a bake-finishing composition containing a heat-curable resin and an oxime sulfonate compound is cured by irradiation with short-wavelength light. Japanese Patent Kokai 61-251652 discloses oxime sulfonate compounds having a substituent group such as ethylenically unsaturated polymerizable groups, epoxy group, hydroxy group and the like, and polymers thereof. Japanese Patent Kokai 1-124848 teaches an image-forming method by the use of a photosensitive composition containing a film-forming organic substance, an oxime sulfonate compound and a photosensitive compound having an aromatic group. Japanese Patent Kokai 2-154266 discloses a photoresist composition containing an alkali-soluble resin, oxime sulfonate compound and sensitivity enhancing crosslinking agent. Japanese Patent Kokai 2-161444 teaches a negative-patterning method by the use of an oxime sulfonate compound. Further, Japanese Patent Kokai 6-67433 discloses a photoresist composition for i-line exposure containing an oxime sulfonate compound.

The oxime sulfonate compounds having a cyano group in the molecule disclosed in the above-mentioned patent documents include:

α-(p-toluenesulfonyloxyimino)phenyl acetonitrile;
α-(4-chlorobenzenesulfonyloxyimino)phenyl acetonitrile;
α-(4-nitrobenzenesulfonyloxyimino)phenyl acetonitrile;
α-(4-nitro-2-trifluoromethylbenzenesulfonyloxyimino) phenyl acetonitrile;
α-(benzenesulfonyloxyimino)-4-chlorophenyl acetonitrile;
α-(benzenesulfonyloxyimino)-2,4-dichlorophenyl acetonitrile;
α-(benzenesulfonyloxyimino)-2,6-dichlorophenyl acetonitrile;
α-(benzenesulfonyloxyimino)-4-methoxyphenyl acetonitrile;
α-(2-chlorobenzenesulfonyloxyimino)-4-methoxyphenyl acetonitrile;
α-(benzenesulfonyloxyimino)-2-thienyl acetonitrile;
α-(4-dodecylbenzenesulfonyloxyimino)phenyl acetonitrile;
α-(p-toluenesulfonyloxyimino)-4-methoxyphenyl acetonitrile;
α-(4-dodecylbenzenesulfonyloxyimino)-4-methoxyphenyl acetonitrile;
α-(p-toluenesulfonyloxyimino)-3-thienyl acetonitrile; and the like.

The molecules of these sulfonate compounds are susceptible to scission of the sulfonate ester linkage by irradiation with actinic rays to generate a corresponding sulfonic acid so that they are useful as an acid-generating agent in the chemical-sensitization photoresist compositions.

It should be mentioned that, while a sulfonic acid is generated from the oxime sulfonate compound by exposure to light, the number of the sulfonic acid molecules released from a molecule of the above-named oxime sulfonate compounds is necessarily limited to one, so that the amount of the acid is also limited. When such an oxime sulfonate compound is used as an acid-generating agent in a negative-working photoresist composition, accordingly, no satisfactory patterned resist layer can be obtained because the width of a line-patterned resist layer cannot be broad enough at the top and the dimensional fidelity and heat resistance of the patterned resist layer cannot be as high as desired along with a relatively low exposure dose latitude.

SUMMARY OF THE INVENTION

The present invention, accordingly, has a primary object to provide novel and improved positive-working and negative-working chemical-sensitization photoresist compositions capable of giving a patterned resist layer having good cross-sectional profile, high dimensional fidelity and excellent heat resistance with excellent photosensitivity and exposure dose latitude.

The present invention further has an object to provide a novel cyano group-containing oxime sulfonate compound which is useful as an acid-generating agent in a chemical-sensitization photoresist composition exhibiting a high efficiency for the generation of an acid upon irradiation with actinic rays.

Thus, the cyano group-containing oxime sulfonate compound of the present invention useful as an acid-generating agent in a chemical-sensitization photoresist composition is a novel compound not known in the prior art nor described in any literature as represented by the general formula $$A[C(CN)=N-O-SO_2-R]_n, \qquad (I)$$

in which each R is, independently from the others, an unsubstituted or substituted monovalent hydrocarbon group, A is a divalent or tervalent organic group and the subscript n is 2, when A is a divalent group, or 3, when A is a tervalent group.

The positive-working chemical-sensitization photoresist composition provided by the present invention comprises, as a uniform solution in an organic solvent:

(a1) an alkali-soluble hydroxy-containing resin, of which at least a part of the hydroxy groups are substituted by acid-dissociable groups so as to decrease the alkali-solubility of the resin in an aqueous alkaline solution; and (b) the cyano group-containing oxime sulfonate compound defined above as an acid-generating agent, of which the subscript n in the general formula (I) is preferably 2.

The negative-working chemical-sensitization photoresist composition provided by the present invention, on the other hand, comprises, as a uniform solution in an organic solvent:

(a2) an alkali-soluble resin or an alkali-soluble hydroxy-containing resin, of which a part of the hydroxy groups are substituted by acid-dissociable groups;

(b) the cyano group-containing oxime sulfonate compound defined above as an acid-generating agent, of which the subscript n in the general formula (I) is preferably 2; and (c) a crosslinking agent which is a compound capable of forming crosslinks in the presence of an acid.

DETAILED DESCRIPTION OF THE PREFERRED EMBODIMENTS

As is described above, each of the positive-working and negative-working photoresist compositions of the invention is characterized by the use of a specific cyano group-containing oxime sulfonate compound as an acid-generating agent, i.e., the component (b). In the positive-working photoresist composition of the invention, an acid is released from the component (b) by exposure to actinic rays so that the acid-dissociable substituent groups in the component (a1) are dissociated so as to increase the solubility of the resist layer in an aqueous alkaline developer solution pattern-wise in the areas exposed to actinic rays. In the negative-working photoresist composition of the invention, on the other hand, the acid-crosslinking ingredient as the component (c) causes crosslinking of the resinous ingredient as the component (a2) when an acid is generated from the acid-generating agent as the component (b) in the resist layer so as to decrease the solubility of the resist layer in an aqueous alkaline developer solution pattern-wise in the areas exposed to actinic rays.

The above-mentioned alkali-soluble resin as the component (a2) is exemplified by novolac resins obtained by the condensation reaction of a phenolic compound such as phenol, m- and p-cresols, xylenols, trimethylphenols and the like, with an aldehyde compound such as formaldehyde in the presence of an acidic catalyst, hydroxystyrene-based resins, e.g., homopolymeric polyhydroxystyrene resins, copolymeric resins of hydroxystyrene and other styrene monomers and copolymeric resins of hydroxystyrene and (meth)acrylic acid or a derivative thereof and (meth)acrylic acid-based resins, e.g., copolymeric resins of (meth)acrylic acid and a derivative thereof.

The alkali-soluble hydroxy-containing resin from which the component (a1) is derived by substitution of acid-dissociable groups for at least a part of the hydroxy groups is exemplified by homopolymeric polyhydroxystyrene resins, copolymeric resins of hydroxystyrene and other styrene monomers, copolymeric resins of hydroxystyrene and (meth)acrylic acid or a derivative thereof and copolymeric resins of (meth)acrylic acid and a derivative thereof having carboxylic hydroxy groups.

The above-mentioned styrene monomers to be copolymerized with hydroxystyrene include styrene, α-methylstyrene, p- and o-methylstyrenes, p-methoxystyrene, p-chlorostyrene and the like. The above-mentioned derivatives of (meth)acrylic acid to be copolymerized with hydroxystyrene or (meth)acrylic acid include methyl (meth)acrylate, ethyl (meth)acrylate, 2-hydroxyethyl (meth)acrylate, 2-hydroxypropyl (meth)acrylate, (meth)acrylamide, (meth)acrylonitrile and the like.

The acid-dissociable groups substituting for at least a part of the hydroxy groups in the above-mentioned alkali-soluble hydroxy-containing resins are exemplified by alkoxycarbonyl groups such as tert-butoxycarbonyl group and tert-amyloxycarbonyl group, tertiary alkyl groups such as tert-butyl group, alkoxyalkyl groups such as ethoxyethyl group and methoxypropyl group, acetal groups such as tetrahydropyranyl group and tetrahydrofuranyl group, benzyl group, trimethylsilyl group and so on.

The degree of substitution of the above-mentioned acid-dissociable groups for the hydroxy groups in the hydroxy-containing resin is usually in the range from 1 to 60% or, preferably, from 10 to 50%.

In the positive-working chemical-sensitization photoresist composition of the present invention, the resinous ingredient as the component (a1) is preferably a polyhydroxystyrene resin substituted by tert-butoxycarbonyl groups, tetrahydropyranyl group or alkoxyalkyl groups such as ethoxyethyl and methoxypropyl groups for a part of the hydroxy groups in the starting polyhydroxystyrene resin or a combination of these resins.

In the negative-working chemical-sensitization photoresist composition of the present invention, the alkali-soluble resinous ingredient as the component (a2) used in combination with the acid-crosslinking agent as the component (c) can be selected from the group consisting of novolac resins, hydroxystyrene-based polymeric resins and (meth)acrylic acid-based polymeric resins as well as these resins substituted by acid-dissociable groups for a part of the hydroxy groups in the resins. The component (a2) is preferably a cresol novolac resin, polyhydroxystyrene resin, a copolymeric resin of hydroxystyrene and styrene or a resin obtained by substitution of tert-butoxycarbonyl groups for a part of the hydroxy groups in a polyhydroxystyrene resin.

The acid-crosslinking agent as the component (c) compounded in the negative-working chemical-sensitization photoresist composition of the invention in combination with the above-described component (a2) can be selected from those known in the conventional negative-working chemical-sensitization photoresist compositions without particular limitations. Examples of the component (c) include amino resins having hydroxy and/or alkoxy groups such as melamine resins, urea resins, guanamine resins, acetoguanamine resins, benzoguanamine resins, glycoluryl-formaldehyde resins, succinylamide-formaldehyde resins, ethyleneurea-formaldehyde resins and the like. These resins can be easily obtained by the reaction of melamine, urea, guanamine, acetoguanamine, benzoguanamine, glycoluryl, succinylamide or ethyleneurea in boiling water with formaldehyde to effect methylolation optionally followed by an alkoxylation reaction with a lower alcohol. Commercial products of several grades are available for these resins including those sold under the trade names of Nicalacs Mx-750, Mw-30 and Mx-290 (each a product by Sanwa Chemical Co.).

Besides the above-mentioned resinous compounds, the component (c) can be selected from the group consisting of benzene compounds having alkoxy groups such as 1,3,5-tris(methoxymethoxy)benzene, 1,2,4-tris(isopropoxymethoxy)benzene and 1,4-bis(sec-butoxymethoxy)benzene and phenol compounds having hydroxy and/or alkoxy groups such as 2,6-di(hydroxymethyl)p-cresol and 2,6-di(hydroxymethyl)-p-tert-butyl phenol.

The above-described acid-crosslinking agents can be used in the negative-working photoresist composition of the invention either singly or as a combination of two kinds or more according to need.

The amount of the acid-crosslinking agent as the component (c) in the negative-working chemical-sensitization photoresist composition of the invention is usually in the range from 3 to 70 parts by weight or, preferably, in the range from 5 to 50 parts by weight per 100 parts by weight of the component (a2). When the amount of the component (c) is too small, the photoresist composition cannot be imparted with high photosensitivity while, when the amount thereof is too large, the resist layer formed from the photoresist composition on a substrate surface cannot be uniform along with a decrease in the developability not to give a patterned resist layer of high quality.

The alkali-soluble resin for the component (a1) or (a2) should preferably have an average molecular weight in the range from 2000 to 20000. Further, it is preferable that the alkali-soluble resin has a molecular weight distribution as narrow as possible in order to obtain a patterned resist layer of high quality in the pattern resolution and heat resistance of the resist layer. The molecular weight distribution of the resin can be represented by the ratio of the weight-average molecular weight Mw to the number-average molecular weight Mn, i.e., Mw:Mn, which should preferably be 3.5 or smaller or, more preferably, 3.0 or smaller for novolac resins and preferably should be 3.5 or smaller or, more preferably, 2.5 or smaller for polyhydroxystyrene-based resins.

The inventive chemical-sensitization photoresist composition, which is either of the positive-working type or of the negative-working type, is characterized by the use of a very specific acid-generating agent which is a novel cyano group-containing oxime sulfonate compound represented by the general formula (I) given before, in which R is an unsubstituted or substituted monovalent hydrocarbon group, A is a divalent or tervalent organic group and the subscript n is 2, when A is divalent, or 3, when A is tervalent, or, in particular, 2.

The monovalent hydrocarbon group denoted by R is an aryl group having 6 to 14 carbon atoms or a non-aromatic hydrocarbon group including alkyl groups, cycloalkyl groups, alkenyl groups and cycloalkenyl groups having 12 or less carbon atoms. When R is a substituted hydrocarbon group, the substituent group can be a halogen atom, hydroxy group, alkoxy group or acyl group or, in particular, a halogen atom when R is an alkyl group having 1 to 4 carbon atoms.

The above-mentioned aryl group having 6 to 14 carbon atoms is exemplified by phenyl, tolyl, methoxyphenyl, xylyl, biphenyl, naphthyl and anthryl groups. The above-mentioned alkyl group, which can be straightly linear or branched, having 1 to 12 carbon atoms is exemplified by methyl, ethyl, propyl, isopropyl, n-butyl, sec-butyl, tert-butyl, n-pentyl, n-octyl and n-dodecyl groups. The alkenyl group is exemplified by ethenyl, propenyl, butenyl, butadienyl, hexenyl and octadienyl groups. The cycloalkyl group is exemplified by cyclopentyl, cyclohexyl, cyclooctyl and cyclododecyl groups. The cycloalkenyl group is exemplified by 1-cyclobutenyl, 1-cyclopentenyl, 1-cyclohexenyl, 1-cycloheptenyl and 1-cyclooctenyl groups.

The above-described monovalent aromatic or non-aromatic hydrocarbon groups as R in the general formula (I) can be substituted by substituents for one or more of the hydrogen atoms in a molecule. The substituent is selected from the group consisting of halogen atoms, i.e., atoms of fluorine, chlorine and bromine, hydroxy group, alkoxy groups and acyl groups. Halogenated alkyl groups as a class of the non-aromatic substituted hydrocarbon groups should preferably have 1 to 4 carbon atoms including chloromethyl, trichloromethyl, trifluoromethyl and 2-bromopropyl groups.

The group denoted by A in the general formula (I) is a divalent or tervalent organic group which is preferably an aliphatic or aromatic hydrocarbon group. More preferably, the group denoted by A is an o-, m- or p-phenylene group.

Since the cyano group-containing oxime sulfonate compound of the invention, which can be used as an acid-generating agent in the inventive photoresist composition, has two or three sulfonate ester groups per molecule, two or three molecules of sulfonic acid are generated from a molecule of the sulfonate compound by exposure to actinic rays so that the efficiency of acid generation can be high so much with the same exposure dose. Each of the groups denoted by R in the general formula (I) representing the oxime sulfonate compound is preferably a halogen-substituted or unsubstituted non-aromatic hydrocarbon group because the heat resistance of the patterned photoresist layer is somewhat decreased as a trend when the group R or hence the oxime sulfonate molecule is bulky. In addition, a halogen-substituted or unsubstituted non-aromatic hydrocarbon group has low absorptivity to ultraviolet light so that the transparency of the photoresist layer to the exposure light is little decreased even by increasing the amount of the acid-generating agent in the photoresist composition with an object to increase the photosensitivity of the composition along with advantageous effects on the pattern resolution and cross-sectional profile of the patterned resist layer. When the inventive photoresist composition is patternwise exposed to KrF excimer laser beams having a wavelength of 248 nm, the group denoted by A in the general formula (I) is preferably an alkylene group in view of the high transparency of alkylene groups to the light of this wavelength, while a phenylene group is preferred as the group A when the photoresist composition is for pattern-wise exposure to i-line ultraviolet light having a wavelength of 365 nm.

Further, the halogen-substituted or unsubstituted non-aromatic hydrocarbon group as the group denoted by R is preferably a halogen-substituted or unsubstituted alkyl group having 1 to 4 carbon atoms in consideration of the high diffusibility of the acid generated from the acid-generating agent in the resist layer in the post-exposure baking treatment after pattern-wise exposure of the resist layer to actinic rays.

Examples of the cyano group-containing oxime sulfonate compound of the invention, which can be the acid-generating agent as the component (b) in the inventive photoresist composition, include those expressed by the following structural formulas:

Me—SO₂—O—N═C(CN)—pPn—C(CN)═N—O—SO₂—Me,

Me—SO₂—O—N═C(CN)—mPn—C(CN)═N—O—SO₂—Me,

Et—SO₂—O—N═C(CN)—pPn—C(CN)═N—O—SO₂—Et,

Bu—SO₂—O—N═C(CN)—mPn—C(CN)═N—O—SO₂—Bu,

Bu—SO₂—O—N═C(CN)—pPn—C(CN)═N—O—SO₂—Bu,

CF₃—SO₂—O—N═C(CN)—pPn—C(CN)═N—O—SO₂—CF₃,

CF₃—SO₂—O—N═C(CN)—mPn—C(CN)═N—O—SO₂—CF₃,

Ch—SO₂—O—N═C(CN)—pPn—C(CN)═N—O—SO₂—Ch,

Ph—SO₂—O—N═C(CN)—pPn—C(CN)═N—O—SO₂—Ph,

Me—pPh—SO₂—O—N═C(CN)—pPn—C(CN)═N—O—SO₂—pPn—Me,

Me—pPn—SO₂O—N═C(CN)—mPn—C(CN)═N—O—SO₂—pPn—Me,

Me—O—pPn—SO₂—O—N═C(CN)—mPn—C(CN)═N—O—SO₂—pPn—O—Me,

Me—SO₂—O—N═C(CN)—(CH₂)₃—C(CN)═N—O—SO₂—Me, and

Bu—SO₂—O—N═C(CN)—(CH₂)₅—C(CN)═N—O—SO₂—Bu as the examples of the compound in which the linking group A in the general formula (I) is a divalent hydrocarbon group such as phenylene and alkylene groups; and

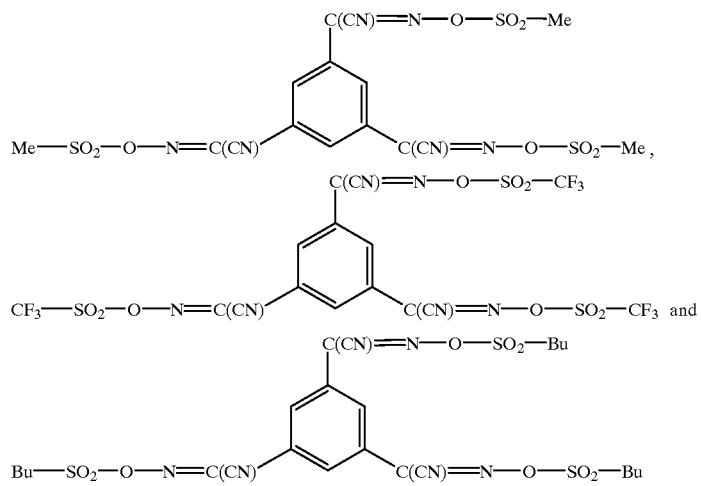

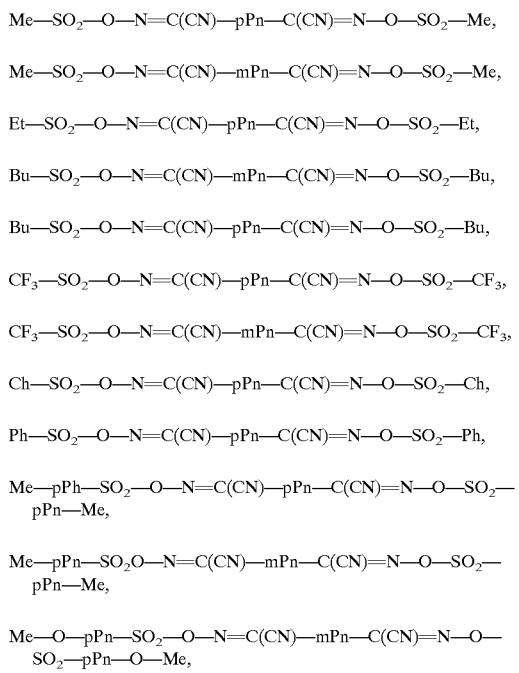

as the examples of the compound in which the linking group A in the general formula (I) is a tervalent hydrocarbon group, in which Me, Et, Bu, Ch and Ph are methyl, ethyl, butyl, cyclohexyl and phenyl groups, respectively, and mPn and pPn are m-phenylene and p-phenylene groups, respectively.

The above-named oxime sulfonate compounds can be used either singly or as a combination of two kinds or more according to need as the acid-generating agent, i.e., component (b), in the chemical-sensitization photoresist composition of the invention.

The amount of the cyano group-containing oxime sulfonate compound as the acid-generating agent, i.e., component (b), in the inventive chemical-sensitization photoresist composition is in the range from 0.1 to 30 parts by weight or, preferably, from 1 to 20 parts by weight per 100 parts by weight of the component (a1), when the photoresist composition is of the positive-working type, or the total amount of the components (a2) and (c), when the photoresist composition is of the negative-working type, in respect of obtaining good balance of film-forming behavior of the composition, image-forming behavior and developability. When the amount of the component (b) is too small, complete patterning can hardly be obtained while, when the amount thereof is too large, a decrease is caused in the uniformity of the resist layer formed from the photoresist composition on the substrate surface along with a decrease in the developability of the resist layer after pattern-wise exposure to actinic rays.

The chemical-sensitization photoresist composition of the invention is used preferably in the form of a uniform solution prepared by dissolving the above-described essential components in an organic solvent. Examples of suitable organic solvents include ketone compounds such as acetone, methyl ethyl ketone, cyclohexanone, methyl isoamyl ketone and 2-heptanone; monoethers of polyhydric alcohols such as monomethyl, monoethyl, monopropyl, monobutyl and monophenyl ethers of ethylene glycol, diethylene glycol, propylene glycol or dipropylene glycol and monoacetates thereof; cyclic ethers such as dioxane; ester compounds such as methyl lactate, ethyl lactate, methyl acetate, ethyl acetate, butyl acetate, methyl pyruvate, ethyl pyruvate, methyl methoxypropionate and ethyl ethoxypropionate; and amide compounds such as N,N-dimethyl formamide, N,N-dimethyl acetamide and N-methyl-2-pyrrolidone. These organic solvents can be used either singly or as a mixture of two kinds or more according to need.

Besides the above-described essential components, it is optional that the photoresist composition of the present invention is admixed with various kinds of known additives used in conventional photoresist compositions and having compatibility with the essential ingredients including auxiliary resins to modify or improve the properties of the resist layer, plasticizers, stabilizers, coloring agents, surface-active agents, carboxylic acid compounds, amine compounds and the like.

The procedure for the photolithographic patterning of a resist layer using the photoresist composition of the invention can be conventional as in the prior art technology. In the first place, namely, a substrate such as a semiconductor silicon single crystal wafer is coated with the photoresist composition in the form of a solution by using a suitable coating machine such as a spinner followed by drying to form a uniform coating film of the photoresist composition, which is then exposed pattern-wise to actinic rays such as ultraviolet light, deep-ultraviolet light, excimer laser beams and the like through a pattern-bearing photomask or irradiated pattern-wise with electron beams by scanning according to the desired pattern to form a latent image of the pattern followed by a post-exposure baking treatment. The latent image of the pattern formed in the resist layer is then developed by dipping the substrate in an aqueous alkaline developer solution such as an aqueous solution of tetramethylammonium hydroxide in a concentration of 1 to 10% by weight followed by rinse with water and drying to give a resist layer patterned with good fidelity to the photomask pattern.

In the following, the present invention directed to the novel cyano group-containing oxime sulfonate compounds and chemical-sensitization photoresist compositions is illustrated in more detail by way of Examples and Comparative Examples, in which the term of "parts" always refers to "parts by weight".

EXAMPLE 1

A cyano group-containing oxime sulfonate compound expressed by the formula

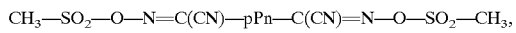

CH₃—SO₂—O—N=C(CN)—pPn—C(CN)=N—O—SO₂—CH₃, in which pPn is a p-phenylene group, was synthetically prepared in the following manner. Thus, 20.0 g (0.093 mole) of bis(α-hydroxyimino)-p-phenylene diacetonitrile and 22.6 g (0.233 mole) of triethylamine dissolved in 200 ml of tetrahydrofuran were introduced into a reaction vessel to form a uniform solution which was chilled to and kept at −5° C. and to which 26.7 g (0.233 mole) of mesyl chloride were added dropwise under agitation over a period of 2 hours followed by further continued agitation at −5 ° C. for 2 hours and then at about 25° C. for 20 hours to complete the reaction. The reaction mixture was subjected to distillation at 30° C. under reduced pressure for the removal of tetrahydrofuran to obtain a crude product. A 22 g portion thereof was subjected to purification by repeating recrystallization from acetonitrile to obtain 12.5 g of a white crystalline compound having a melting point at 263° C. as the product which could be identified to be the above-mentioned target compound as being supported by the analytical results shown below. The above-mentioned yield of the product corresponds to 36.3% of the theoretical value.

The infrared absorption spectrum of the product compound had absorption bands having peaks at wave numbers of 769 cm⁻¹, 840 cm⁻¹, 1189 cm⁻¹, 1382 cm⁻¹ and 2240 cm⁻¹. The proton nuclear magnetic resonance (¹H-NMR) spectrum of the compound in dimethyl sulfoxide-d₆ had absorptions at δ values of 3.68 ppm and 8.15 ppm. The ultraviolet absorption spectrum of the compound in tetrahydrofuran as the solvent had absorption bands having peaks at wavelengths λ$_{max}$ of 220 nm and 301 nm with molar absorption coefficients of 7900 and 12200, respectively.

EXAMPLE 2

A cyano group-containing oxime sulfonate compound expressed by the formula

CH₃—SO₂—O—N=C(CN)—mPn—C(CN)=N—O—SO₂—CH₃, in which mPn is a m-phenylene group, was synthetically prepared in substantially the same manner as in Example 1 excepting for the replacement of the bis(α-hydroxyimino)-p-phenylene diacetonitrile with the same amount of bis(α-hydroxyimino)-m-phenylene diacetonitrile. A 30 g portion of the crude reaction product was subjected to purification by repeating recrystallization from acetonitrile to obtain 25.8 g of a white crystalline compound having a melting point at 196° C. as the product which could be identified to be the above-mentioned target compound as being supported by the analytical results shown below. The above-mentioned yield of the product corresponds to 72.0% of the theoretical value.

The infrared absorption spectrum of the product compound had absorption bands having peaks at wave numbers of 782 cm⁻¹, 844 cm⁻¹, 1191 cm⁻¹, 1382 cm⁻¹ and 2238 cm⁻¹. The proton nuclear magnetic resonance (¹H-NMR) spectrum of the compound in dimethyl sulfoxide-d₆ had absorptions at δ values of 3.65 ppm, 7.89 ppm, 8.27 ppm and 8.29 ppm. The ultraviolet absorption spectrum of the compound in tetrahydrofuran as the solvent had absorption bands having peaks at wavelengths λ$_{max}$ of 211 nm and 269 nm with molar absorption coefficients of 6500 and 12100, respectively.

EXAMPLE 3

A cyano group-containing oxime sulfonate compound expressed by the formula

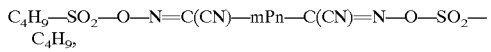

C₄H₉—SO₂—O—N=C(CN)—mPn—C(CN)=N—O—SO₂—C₄H₉, in which mPn is a m-phenylene group, was synthetically prepared in substantially the same manner as in Example 1 excepting for the replacement of the bis(α-hydroxyimino)-p-phenylene diacetonitrile with the same amount of bis(α-hydroxyimino)-m-phenylene diacetonitrile and replacement of 26.7 g of mesyl chloride with 36.3 g (0.233 mole) of 1-butanesulfonyl chloride. A 32 g portion of the crude reaction product was subjected to purification by repeating recrystallization from acetonitrile to obtain 20.5 g of a white crystalline compound having a melting point at 98° C. as the product which could be identified to be the above-mentioned target compound as being supported by the analytical results shown below. The above-mentioned yield of the product corresponds to 48.5% of the theoretical value.

The infrared absorption spectrum of the product compound had absorption bands having peaks at wave numbers of 783 cm$^{-1}$, 844 cm$^{-1}$, 1191 cm$^{-1}$, 1382 cm$^{-1}$ and 2239 cm$^{-1}$. The proton nuclear magnetic resonance ($^1$H-NMR) spectrum of the compound in acetone-d$_6$ had absorptions at δ values of 0.98 ppm, 1.52 ppm, 1.92 ppm, 3.70 ppm, 7.91 ppm, 8.27 ppm and 8.40 ppm. The ultraviolet absorption spectrum of the compound in tetrahydrofuran as the solvent had absorption bands having peaks at wavelengths λ$_{max}$ of 211 nm and 268 nm with molar absorption coefficients of 7100 and 13500, respectively.

EXAMPLE 4

A cyano group-containing oxime sulfonate compound expressed by the formula

in which mPn is a m-phenylene group and pPn is a p-phenylene group, was synthetically prepared in the following manner. Thus, 10.0 g (0.0465 mole) of bis(α-hydroxyimino)-m-phenylene diacetonitrile and 11.3 g (0.116 mole) of triethylamine dissolved in 200 ml of tetrahydrofuran were introduced into a reaction vessel to form a uniform solution which was chilled to and kept at −5° C. and to which 22.1 g (0.116 mole) of p-toluenesulfonyl chloride were added dropwise under agitation over a period of 2 hours followed by further continued agitation at −5° C. for 2 hours and then at about 25° C. for 20 hours to complete the reaction. The reaction mixture was subjected to distillation at 30° C. under reduced pressure for the removal of tetrahydrofuran to obtain a crude product. A 12 g portion thereof was subjected to purification by repeating recrystallization from acetonitrile to obtain 10.0 g of a white crystalline compound having a melting point at 205° C. as the product which could be identified to be the above-mentioned target compound as being supported by the analytical results shown below. The above-mentioned yield of the product corresponds to 41.3% of the theoretical value.

The infrared absorption spectrum of the product compound had absorption bands having peaks at wave numbers of 773 cm$^{-1}$, 836 cm$^{-1}$, 1197 cm$^{-1}$, 1394 cm$^{-1}$ and 2237 cm$^{-1}$. The proton nuclear magnetic resonance ($^1$H-NMR) spectrum of the compound in dimethyl sulfoxide-d$_6$ had absorptions at δ values of 2.42 ppm, 7.52 ppm, 7.77 ppm and 7.98 ppm. The ultraviolet absorption spectrum of the compound in tetrahydrofuran as the solvent had absorption bands having peaks at wavelengths λ$_{max}$ of 230 nm and 270 nm with molar absorption coefficients of 24000 and 17300, respectively.

EXAMPLE 5

A cyano group-containing oxime sulfonate compound expressed by the formula

CF$_3$—SO$_2$—O—N=C(CN)—mPn—C(CN)=N—O—SO$_2$—CF$_3$, in which mPn is a m-phenylene group, was synthetically prepared in substantially the same manner as in Example 2 excepting for the replacement of 26.7 g of the mesyl chloride with 64.7 g (0.233 mole) of trifluoromethanesulfonic acid anhydride.

EXAMPLE 6

A cyano group-containing oxime sulfonate compound expressed by the formula

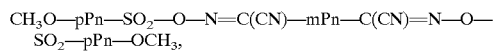

in which mPn is a m-phenylene group and pPn is a p-phenylene group, was synthetically prepared in substantially the same manner as in Example 4 excepting for the replacement of 22.1 g of the p-toluenesulfonyl chloride with 24.0 g (0.116 mole) of 4-methoxybenzenesulfonyl chloride.

EXAMPLE 7

A negative-working photoresist composition was prepared by dissolving, in a mixture of 384 parts of propyleneglycol monomethyl ether acetate and 96 parts of N-methyl-2-pyrrolidone, 100 parts of a copolymeric resin of hydroxystyrene and styrene having a weight-average molecular weight of 2500 and 15 parts of a melamine resin (Mw-30, a product by Sanwa Chemical Co.) and further admixing the solution with 3 parts of the oxime sulfonate compound prepared in Example 2 as an acid-generating agent.

The thus-prepared photoresist solution was applied onto the surface of a silicon wafer on a spinner followed by drying on a hotplate at 90° C. for 90 seconds to give a photoresist layer having a thickness of 1.0 μm. The resist layer was exposed pattern-wise to i-line ultraviolet light of 365 nm wavelength through a Levenson phase-shift mask on a minifying projection exposure machine (Model NSR-2005i10D, manufactured by Nikon Co.) and subjected to a post-exposure baking treatment at 100° C. for 90 seconds followed by a development treatment in a 2.38% by weight aqueous solution of tetramethylammonium hydroxide at 23° C. for 65 seconds, rinse with water for 30 seconds and drying to give a line-and-space pattern of the resist layer.

The cross-sectional profile of a line-and-space pattern of the resist layer having a line width of 0.30 μm was excellently orthogonal standing upright on the substrate surface as examined on a scanning electron microscopic photograph. The exposure dose latitude as expressed by Eop/Eg was 1.70, in which Eop is the exposure dose required for the reproduction of a line-and-space pattern of 0.30 μm line width with a line width:space width of 1:1, and Eg is the exposure dose for the incipient pattern formation in the exposed area of a line-and-space pattern of 0.30 μm line width.

COMPARATIVE EXAMPLE 1

The experimental procedure for the preparation and testing of a negative-working photoresist composition was substantially the same as in Example 7 described above excepting for the replacement of the oxime sulfonate compound prepared in Example 2 with the same amount of α-(p-toluenesulfonyloxyimino)-4-methoxyphenyl acetonitrile.

The results of the evaluation tests were that the cross-sectional profile of a line-and-space patterned resist layer having a line width of 0.30 μm was not orthogonal but had a width narrowed toward the top of the cross-section and the exposure dose latitude Eop/Eg was 1.60.

EXAMPLE 8

A negative-working photoresist composition was prepared by dissolving, in 270 parts of propyleneglycol monomethyl ether acetate, 100 parts of a cresol novolac resin as a condensation product of m-cresol and formaldehyde having a weight-average molecular weight of 10000 and 10 parts of a melamine resin (Mw-30, a product by Sanwa Chemical Co.) and further admixing the solution with 1.5 parts of the oxime sulfonate compound prepared in Example 2 as an acid-generating agent.

The thus-prepared photoresist solution was applied onto the surface of a silicon wafer on a spinner followed by drying on a hotplate at 90° C. for 90 seconds to give a photoresist layer having a thickness of 2.0 μm. The resist layer was exposed pattern-wise to i-line ultraviolet light of 365 nm wavelength on a minifying projection exposure machine (Model NSR-2005i10D, manufactured by Nikon Co.) and subjected to a post-exposure baking treatment at 100° C. for 90 seconds followed by a development treatment in a 2.38% by weight aqueous solution of tetramethylammonium hydroxide at 23° C. for 65 seconds, rinse with water for 30 seconds and drying to give a line-and-space pattern of the resist layer.

As a measure of the photosensitivity of the photoresist composition, the minimum exposure dose was measured for the formation of a line-and-space pattern of 0.80 μm line width in a line:space width ratio of 1:1 to find an exposure dose of 75 mJ/cm$^2$.

A scanning electron microscopic examination was undertaken for the cross-sectional profile of a line-patterned resist layer having a line width of 0.80 μm by taking a microscopic photograph to find that the cross-sectional profile was excellently orthogonal standing upright on the substrate surface. The ratio of the exposure dose with which a line-and-space pattern of 1 μm line width could be reproduced to have a line:space width ratio of 1:1 to the above-mentioned exposure dose as a measure of the photosensitivity was 1.15 which could be a measure for the dimensional fidelity of pattern reproduction. Further, the heat stability of the patterned resist layer was examined by heating the resist layer on a hotplate to determine the lowest temperature for incipient flowing of a line-and-space pattern of 0.8 μm line width to obtain a temperature of 200° C.

COMPARATIVE EXAMPLE 2

The experimental procedure for the preparation of a photoresist composition was substantially the same as in Example 8 described above excepting for the replacement of 1.5 parts of the oxime sulfonate compound prepared in Example 2 with 3 parts of α-(p-toluenesulfonyloxyimino) phenyl acetonitrile.

As a result of the evaluation tests of the composition undertaken in the same manner as in the preceding examples, the photosensitivity thereof was found to be 300 mJ/cm$^2$. The cross-sectional profile of a line-and-space patterned resist layer having a line width of 0.80 μm was not orthogonal but had a width narrowed toward the top of the cross-section. The dimensional fidelity of the patterned resist layer was 1.35 and the temperature for heat resistance was 140° C.

EXAMPLE 9

The experimental procedure for the preparation of a photoresist composition was substantially the same as in Example 8 described above excepting for the replacement of the oxime sulfonate compound prepared in Example 2 with the same amount of another oxime sulfonate compound prepared in Example 3.

As a result of the evaluation tests of the composition undertaken in the same manner as in the preceding examples, the photosensitivity thereof was found to be 65 mJ/cm$^2$. The cross-sectional profile of a line-and-space patterned resist layer having a line width of 0.80 μm was orthogonal standing upright on the substrate surface. The dimensional fidelity of the patterned resist layer was 1.18 and the temperature for heat resistance was 200° C.

EXAMPLE 10

A positive-working photoresist composition was prepared by dissolving, in 400 parts of propyleneglycol monomethyl ether acetate, 30 parts of a first polyhydroxystyrene substituted by tert-butoxycarbonyloxy groups for 39% of the hydroxy groups and having a weight-average molecular weight of 8000 and a molecular weight distribution Mw:Mn of 1.5, 70 parts of a second polyhydroxystyrene substituted by ethoxyethoxy groups for 39% of the hydroxy groups and having a weight-average molecular weight of 8000 and a molecular weight distribution Mw:Mn of 1.5, 2 parts of the oxime sulfonate compound prepared in Example 2 as an acid-generating agent, 0.3 part of triethylamine, 0.2 part of salicylic acid and 5 parts of N,N-dimethylacetamide followed by filtration of the solution through a membrane filter of 0.2 μm pore diameter.

This photoresist solution was applied to the surface of a silicon wafer on a spinner followed by drying on a hotplate at 80° C. for 90 seconds to form a dried photoresist layer having a thickness of 0.7 μm, which was exposed pattern-wise on a minifying projection exposure machine (Model NSR-2005EX8A, manufactured by Nikon Co.) in doses stepwise increased with increments of each 1 mJ/cm$^2$ by varying the exposure time followed by a post-exposure baking treatment at 110° C. for 90 seconds and developed with a 2.38% by weight aqueous solution of tetramethylammonium hydroxide at 23° C. for 65 seconds followed by rinse with water for 30 seconds and drying. Recording was made there for the minimum exposure dose in mJ/cm$^2$, which was 4 mJ/cm$^2$ in this case, as a measure of the sensitivity by which the resist layer in the exposed areas was completely dissolved away in the development treatment.

A scanning electron microscopic photograph was taken of the cross-sectional profile of the patterned resist line of 0.25 μm width to find that the cross-sectional profile was excellently orthogonal standing upright on the substrate surface.

Further, the heat stability of the patterned resist layer was tested by heating the resist layer on a hot plate to determine the lowest temperature for incipient flowing of a line-and-space pattern of 100 μm line width but no flow of the line-patterned resist layer could be detected at a temperature of 120° C.

What is claimed is:

1. A negative-working chemical-sensitization photoresist composition which comprises, as a uniform solution in an organic solvent:

(a2) an alkali-soluble resin or an alkali-soluble hydroxy-containing resin, of which a part of the hydroxy groups are substituted by acid-dissociable groups;

(b) a cyano group-containing oxime sulfonate compound represented by the general formula $$A[C(CN)=N-O-SO_2-R]_n,$$

in which each R is, independently from the others, an unsubstituted or substituted monovalent hydrocarbon group, A is a divalent or tervalent organic group and the subscript n is 2, when A is a divalent group, or 3, when A is a tervalent group, as an acid-generating agent; and (c) a crosslinking agent which is a compound capable of forming crosslinks in the presence of an acid.

2. The negative-working chemical-sensitization photoresist composition as claimed in claim 1 in which A in the general formula representing the component (b) is a phenylene group.

3. The negative-working chemical-sensitization photoresist composition as claimed in claim 1 in which the crosslinking agent as the component (c) is an amino resin.

4. The negative-working chemical-sensitization photoresist composition as claimed in claim 3 in which the amino resin as the component (c) is a melamine resin or a urea resin.

5. The negative-working chemical-sensitization photoresist composition as claimed in claim 1 in which the amount of the component (c) is in the range from 3 to 70 parts by weight per 100 parts by weight of the component (a2).

6. The negative-working chemical-sensitization photoresist composition as claimed in claim 1 in which the amount of the component (b) is in the range from 0.1 to 30 parts by weight per 100 parts by weight of the total amount of the component (a2) and component (c).

* * * * *